US009433807B2

(12) United States Patent
Albrecht

(10) Patent No.: US 9,433,807 B2
(45) Date of Patent: Sep. 6, 2016

(54) SELF CONTAINED BREATHING APPARATUS ILLUMINATION SYSTEM

(71) Applicant: Michael Joseph Albrecht, Patterson, CA (US)

(72) Inventor: Michael Joseph Albrecht, Patterson, CA (US)

( * ) Notice: Subject to any disclaimer, the term of this patent is extended or adjusted under 35 U.S.C. 154(b) by 191 days.

(21) Appl. No.: 14/494,566

(22) Filed: Sep. 23, 2014

(65) Prior Publication Data

US 2015/0083120 A1 Mar. 26, 2015

Related U.S. Application Data

(60) Provisional application No. 61/960,597, filed on Sep. 23, 2013.

(51) Int. Cl.

| | |
|---|---|
| ***A61M 15/00*** | (2006.01) |
| ***A62B 7/00*** | (2006.01) |
| ***A62B 18/02*** | (2006.01) |
| ***F21V 33/00*** | (2006.01) |
| ***A62B 18/08*** | (2006.01) |
| *F21Y 101/02* | (2006.01) |

(52) U.S. Cl.
CPC ............... *A62B 18/02* (2013.01); *A62B 18/08* (2013.01); *F21V 33/0064* (2013.01); *F21Y 2101/02* (2013.01)

(58) Field of Classification Search
CPC .......... A62B 9/00; A62B 9/006; A62B 9/02; A62B 9/04; A62B 18/02; A62B 18/082; A62B 18/08; F21V 33/0064
See application file for complete search history.

(56) References Cited

U.S. PATENT DOCUMENTS

| | | | | |
|---|---|---|---|---|
| 2,835,250 A * | 5/1958 | Austin | A62B 18/00 | 128/201.15 |
| 4,231,079 A * | 10/1980 | Heminover | A41D 27/085 | 362/106 |
| 5,408,393 A * | 4/1995 | Becker | A42B 3/044 | 362/105 |
| 6,113,243 A * | 9/2000 | Saul | A42B 3/0453 | 345/8 |
| 7,311,413 B1 * | 12/2007 | Barnes | A42B 3/044 | 362/106 |
| 7,520,630 B2 * | 4/2009 | Murphy | A62B 18/08 | 2/410 |
| 2005/0047116 A1 * | 3/2005 | Gagne | A62B 18/08 | 362/105 |
| 2005/0099798 A1 * | 5/2005 | Cugini | F21L 14/00 | 362/105 |

* cited by examiner

*Primary Examiner* — Kristen Matter
(74) *Attorney, Agent, or Firm* — Michael R Shevlin

(57) ABSTRACT

A Self Contained Breathing Apparatus (SCBA) Illumination System utilizing LED (light emitting diode) lights is designed as a modification to attach to a Self Contained Breathing Apparatus (SCBA) mask to provide increased visibility to Professionals working in an Immediately Dangerous to Life or Health (IDLH) environment. The SCBA illumination System can be easily installed on a typical mask. The SCBA illumination System comprises a strip of lights coupled to a power supply comprising a power button and a battery pack. The power button may include a push button or pressure sensor that allows a Professional to activate the push button or pressure sensor easily with a gloved hand. The power source may also include some type of circuitry that powers down the light after a specified amount of time to avoid draining the power source.

19 Claims, 5 Drawing Sheets

SELF CONTAINED BREATHING APPARATUS ILLUMINATION SYSTEM

CROSS-REFERENCE TO RELATED APPLICATIONS

This application claims the benefit under 35 U.S.C. §119 (e) of U.S. Provisional Application No. 61/960,597, filed Sep. 23, 2013; the contents of which are incorporated herein in their entirety.

FIELD

The present invention is generally related to Professionals working in Immediately Dangerous to Life or Health (IDLH) environments of decreased visibility, and more particularly, the present invention adds lights to the Professionals Self Contained Breathing Apparatus (SCBA) for illumination in IDLH environments.

BACKGROUND

Everyday many Professionals, such as Firefighters, Confined Space Specialists and Search and Rescue Personnel, work in Immediately Dangerous to Life or Health (IDLH) environments. Many times these IDLH environments require the Professional to use Personal Protective Equipment (PPE). One piece of PPE that is part of this group is a Self Contained Breathing Apparatus or SCBA that is a device worn by the Professional to provide breathable air in an IDLH environment.

In addition to breathing issues, visibility in IDLH environments is often limited by darkness and/or smoke, and the Professionals have a difficult time seeing without illumination. This limited visibility presents a dangerous situation that may compromise both the safety and effectiveness of the Professionals and their crews. To see in the IDLH environment, the Professionals must use some type of portable lighting, such as a flashlight or other hand held lighting. The portable lighting apparatus can be bulky and difficult to control, i.e., turn on or off in certain environments or situations. For example, attempting to operate a small light switch with gloves on in an environment that requires gloves is difficult. Hand held lights also require use of one hand to hold the light, which is unacceptable to Professionals that require both hands to be free.

Thus there is a need for alternative strategies to increase illumination or visibility in IDLH environments and decrease risk to the Professionals.

SUMMARY

The present invention is directed to a Self Contained Breathing Apparatus (SCBA) Illumination System that can be retrofitted to the mask of a Self Contained Breathing Apparatus (SCBA) mask to provide increased visibility to Professionals working in an Immediately Dangerous to Life or Health (IDLH) environment. The present invention results in heightened awareness of surroundings, improved crew accountability & decreased anxiety which all lead to greater safety and efficiency.

In one embodiment, the SCBA Illumination System is designed to attach to the SCBA mask. The SCBA Illumination System is designed attach to the factory connections for the SCBA mask bolts by replacing the SCBA mask bolts with anchor bolts designed to couple with the SCBA Illumination System. By coupling the SCBA Illumination System proximate the factory parts, the SCBA Illumination System conforms to the SCBA mask shape and does not interfere with the operation of the SCBA mask, such as the breathing apparatus or goggles for example.

In another embodiment, the SCBA Illumination System is designed to replace a current component on a SCBA mask with a lighting system. In the embodiment shown, the SCBA Illumination System is designed as replacement for a factory top molding piece, upper bezel, or metal rim, on the SCBA mask. By coupling the SCBA Illumination System to the SCBA mask by direct replacement of a factory part, the SCBA Illumination System conforms to the mask shape and does not interfere with the operation of the SCBA mask, such as the breathing apparatus or goggles for example.

The SCBA Illumination System also utilizes a touch based switch to operate the lighting that allows the Professional to operate the SCBA Illumination System without removing one's gloves, i.e., turned on or of without removing one's gloves. The present invention also utilizes LED (light emitting diode) lights that allow tier longer use without replacing batteries. Furthermore, LED lights are shock resistant and allow for rugged deployment to a variety of environments that promote short life for filament-based lights. Time-out circuitry may be utilized to turn the light off after a specified amount of time to avoid accidental battery drain. Preventing accidental battery drain provides a more robust apparatus that remains operational longer between battery replacement.

BRIEF DESCRIPTION OF THE DRAWINGS

The present embodiments may be understood from the following detailed description when read in conjunction with the accompanying drawing. It is emphasized that, the various features of the drawing are not necessarily to scale. On the contrary, the dimensions of the various features may be arbitrarily expanded or reduced for clarity.

DETAILED DESCRIPTION

Embodiments of the invention will now be described with reference to the figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

Figure 1:
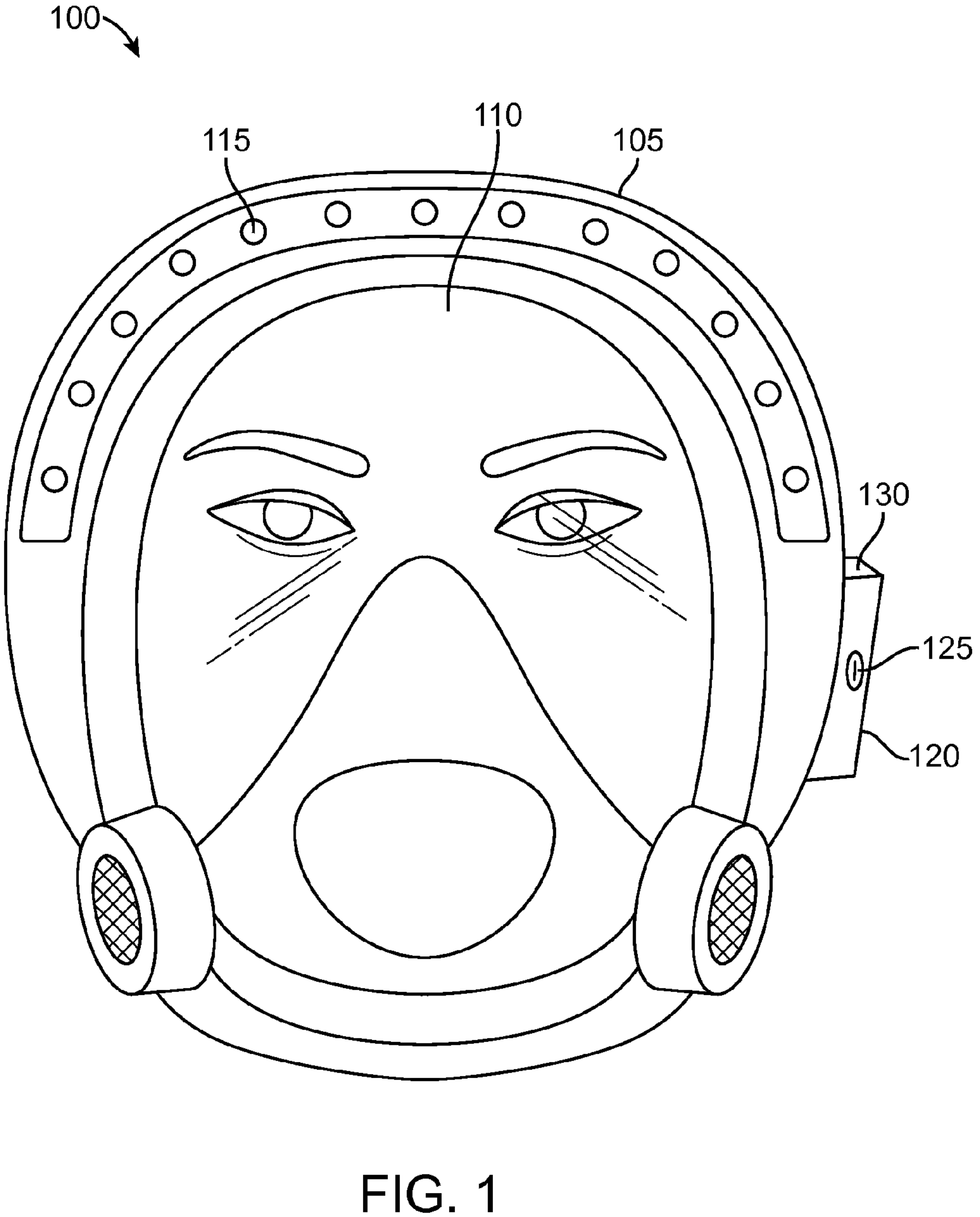
FIG. 1 is a front view and FIG. 2 is a side view showing a Self Contained Breathing Apparatus (SCBA) mask according to the embodiments provided herein.
Figure 2:
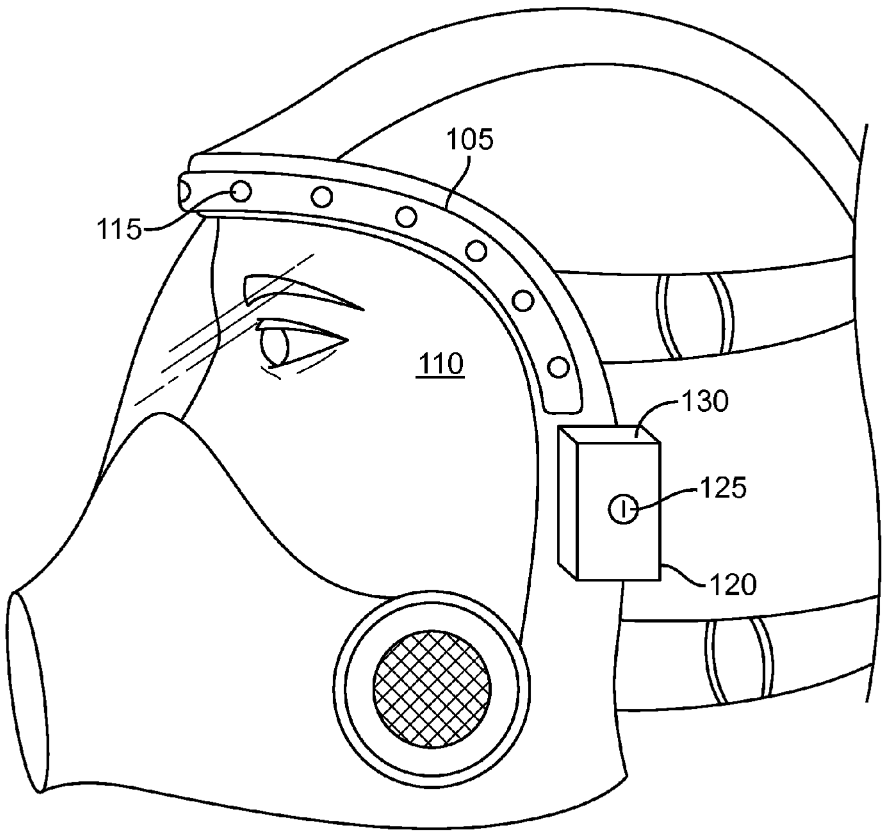

FIG. 1 is a front view and FIG. 2 is a side view showing a Self Contained Breathing Apparatus (SCBA) mask 100 that fits around the head of a Professional and a glass or transparent material facial opening 110 in the front to allow the Professional to see. The present invention adds an illumination feature to the SCBA mask 100. In the embodiment shown, the illumination feature is a Self Contained Breathing Apparatus (SCBA) illumination System 105, shown along a top portion of a SCBA mask 110. In the illustrated embodiment, the SCBA illumination System 105 comprises a strip of LED (light emitting diode) lights 115 coupled to a power supply 120 comprising a power button 125 and a battery pack 130.

The LED lights are very energy efficient and therefore are capable of providing light for long periods of time on small energy sources. The SCBA illumination System 105 provides the Professional with a hands free light source directed forward to illuminate the area generally forward of the Professional, or in whatever direction the Professional is facing by turning the head. The light source comprises a plurality of high intensity light emitting-diodes (LEDs) or lights 115. The LEDs 115 are electrically connected to the power source 120 mounted to the SCBA illumination System 105. A means for controlling the on or off state of the LEDs 115 is provided in the form of the switch or power button 125 connected to the power source or battery pack 130 to power the LEDs 115.

The SCBA illumination System 105 provides a lighting solution for Professionals such that once the invention has been installed on a mask 100, there is no longer a need to utilize a separate light source for emergency situations. The SCBA illumination System 105 can be easily installed on a typical mask 100 with existing mounts 135. By providing the invention using factory connections, the cost for adding a lighting solution can be kept to a minimum. The invention also provides extended life to old SCBA masks by updating them with the added safety associated with a built-in light source.

Figure 3:
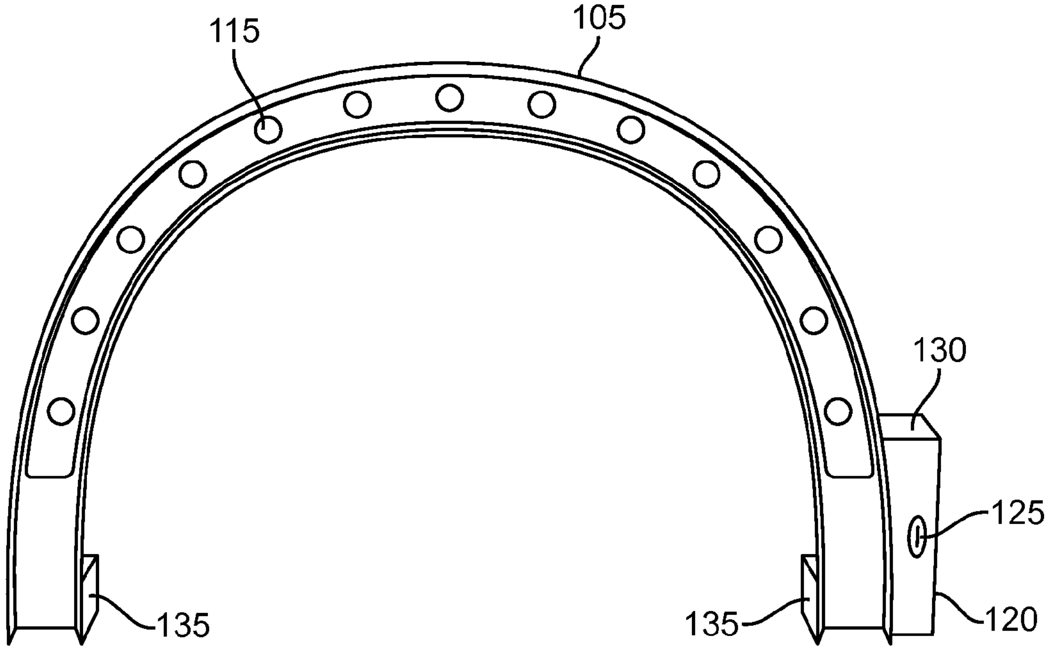
FIG. 3 is a front view and FIG. 4 is a side view of the SCBA illumination System 105 configured to replace a factory top molding piece on the SCBA mask shown in FIGS. 1 and 2, according to the embodiments provided herein.
Figure 4:
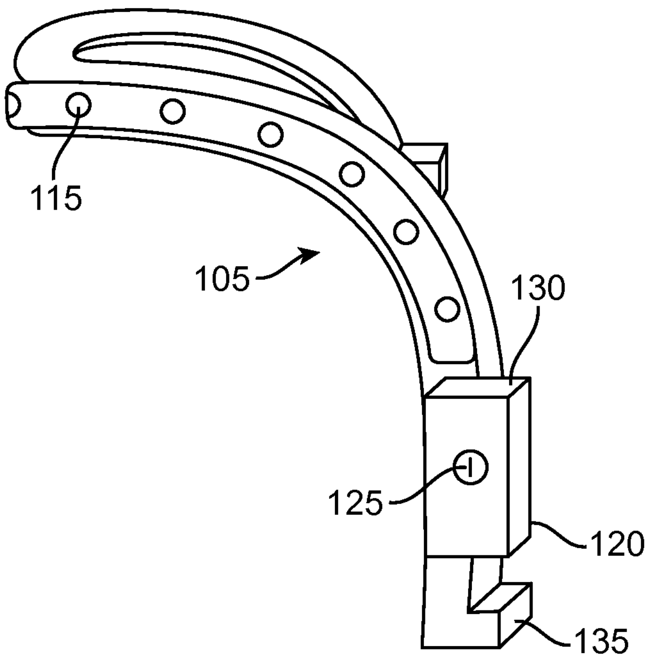

FIG. 3 is a front view and FIG. 4 is a side view of the SCBA illumination System 105. In the present invention, the SCBA illumination System 105 is a modification to an existing SCBA mask 100, either as an add-on part or a replacement part.

Figure 5:
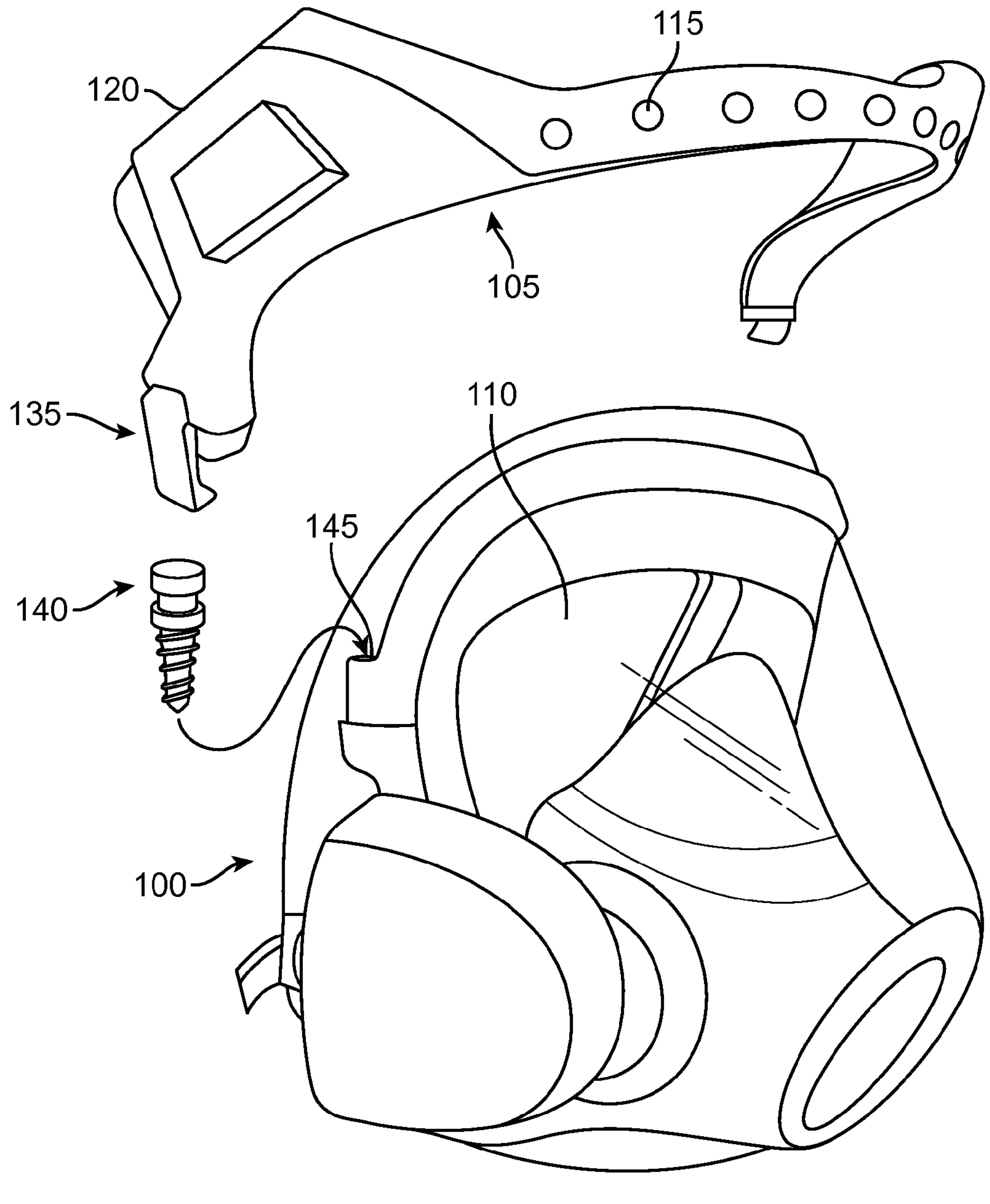
FIG. 5 is an exploded view showing the SCBA illumination System designed to use existing factory mounting points on SCBA mask, according to the embodiments provided herein.

In one embodiment shown in FIG. 5, the SCBA illumination System 105 is designed to use existing factory mounting points 145 on SCBA mask 100 to add the SCBA illumination System 105. In this embodiment, some of the existing screws for the factory top molding piece are removed and replaced by special anchor bolts 140 for attachment of the SCBA illumination System 105. The SCBA illumination System 105 anchors 135 are then attached to the anchor bolts 140. This attachment positions the SCBA illumination System 105 proximate the top molding piece of the SCBA mask 100, adding the illumination features to the SCBA mask 100. The addition of the SCBA illumination System 105 using the existing screw placement is designed and configured so it does not affect the SCBA mask's 100 integrity. This enhancement of adding the SCBA illumination System 105 to the SCBA mask 100 will provide the Professional with increased illumination, visibility, decreasing anxiety, thus keeping the Professional safer and able to work more efficiently and effectively in the IDLH environment.

In another embodiment, the SCBA illumination System 105 is designed to replace an existing factory top molding piece of the SCBA mask 100. Once the factory top molding piece is removed, the SCBA illumination System 105 is placed in the same location using the same attachments. The SCBA illumination System 105 is designed to perform the same structural function as the replaced top molding piece, but now the SCBA mask 100 has been fitted with the illumination features. The SCBA illumination System 105 is designed and configured so it does not affect the SCBA mask's 100 integrity.

The SCBA illumination System 105 is a fully enclosed system that utilizes LED lights 115 along with the power source 120 to power the LED lights 115. The high intensity LEDs can be efficiently arranged so that a minimum number of lights are employed on the SCBA mask 100 while still achieving a well-lit area projecting far forwardly from the SCBA mask 100. The figures show 13 LED lights in the SCBA illumination System 105, but it is contemplated that any number of LED lights may be used In the embodiments shown herein, SCBA illumination System 105 is designed as a modification to a SCBA mask 100. The SCBA illumination System 105 and the electrical conducting path between LEDs are mechanically and integrally disposed within SCBA illumination System 105. The power button 125 may include a push button or pressure sensor that allows for easy operation without requiring a small switch to be activated for example. This allows a Professional to activate the push button or pressure sensor easily with a gloved hand.

A power source 120 is coupled with the LED(s) and is configured as a slender design for unobstructed mounting. One embodiment of the power source is a battery pack 130 containing a battery power source or series of batteries attached at one end to the lights e.g., LEDs or series of LEDs. The power source may be batteries such as a 9 V battery, to provide power to the LED either through direct electrical contact or wiring. In other embodiments, different batteries may be utilized, such as AA or AAA, or coin style type batteries, such as lithium coin cells.

Since accidental activation and subsequent drain of unit power source can be problematic, the power source 120 may include some type of control circuitry that powers down the light after a configurable or specified amount of time.

In various embodiments, the SCBA illumination System 105 comprises a plurality of high intensity light emitting diodes (LED) that radiate light in a broad spectrum so as to appear white to the human eye. In other embodiments, other colors of LEDs may be utilized, such as blue, red, white, yellow, green, amber, or combination thereof, depending on the situation and needs. In some embodiments, the LEDs may also have a flashing mode to provide a signal or warning to other Professionals.

The LEDs can be aligned relative to each other in such a way as to project a beam of light. The beam of light can be contiguous, non-segmented or in a substantially conical shape so that the beam of the LEDs has no dark areas. The LEDs can be parallel to each other or aligned such that the light emitted forms a contiguous pool of light that washes the objects that are illuminated by the beams. Some advantages of LEDs as a light source are durability because they have no filament and are thus much less susceptible to mechanical damage than filament-containing bulbs; relatively cool operation because a filament is not heated to produce light; claimed longevity of 100,000 hours of operation thus obviating the need for replacement and permitting permanent mounting for the life of some products; high light output with low current drain compared to filament-containing bulbs, such that light output equal to or greater than that of a common handheld flashlight can be achieved, and for a longer period of time than with filament bulbs using a similar power source; small power sources such standard size batteries or watch batteries can be used.

In other embodiments, additional or optional LED lights may be designed to fit with other existing screws on the SCBA mask 100. For example, a second strip of LED lights may be designed to be positioned on lower portion of the SCBA mask 100 or may be designed to be incorporated on a nose piece or other location on the SCBA mask 100. The second strip may shine forward, like the SCBA illumination System 105, or may shine in different directions. This feature adds flexibility to the invention by making it possible to shine light in multiple directions at once.

An advantage of the SCBA illumination System 105 is to provide a miniaturized high intensity illumination source, power source and control means that can replace an existing component of SCBA mask 100 in such a way as to add the utility of hands free illumination for seeing in dark or low visibility places in a IDLH environment while preserving the overall aesthetic appearance and utility of the SCBA mask 100.

It is still another advantage of the SCBA illumination System 105 to provide a source of forward directed illumination that can be incorporated into an existing SCBA mask 100 to enhance the intended utility of such specialized headgear by adding an illumination source for the benefit of the Professional.

It is another advantage of the SCBA illumination System 105 that the utility of an illumination device is always readily available when the SCBA mask 100 is worn, rather than being capable of being forgotten or left behind, or being carried on one's person in an inconvenient place.

It is another advantage of the SCBA illumination System 105 to provide portable illumination that is automatically directed along the Professional's line of sight by movement of the Professional's head.

It is another advantage of the SCBA illumination System 105 to provide a robust and reliable source of portable illumination that would not easily break or fail.

It is still another advantage of the SCBA illumination System 105 that the methods of integrating an illumination device into the SCBA mask 100 are generally consistent with the methods of manufacture of the SCBA mask 100, e.g. the SCBA illumination System 105 uses existing screws holes in the mask.

While embodiments and applications of this invention have been shown and described, it would be apparent to those skilled in the art that many more modifications than mentioned above are possible without departing from the inventive concepts herein. The invention, therefore, is not to be restricted except in the spirit of the appended claims.

It is believed that the construction, operation and advantages of this invention will be apparent to those skilled in the art. It is to be understood that the present disclosure is illustrative only and that changes, variations, substitutions, modifications and equivalents will be readily apparent to one skilled in the art and that such may be made without departing from the spirit of the invention as defined by the following claims.

The invention claimed is:

1. A method of adding a Self Contained Breathing Apparatus (SCBA) illumination System to a Self Contained Breathing Apparatus (SCBA) mask, comprising:

removing screws in existing screw locations on the SCBA mask;

inserting anchor bolts into the existing screw locations; and coupling the SCBA illumination System to the anchor bolts.

2. The method according to claim 1, wherein the SCBA illumination System comprises:

a strip of lights;

a power supply comprising a power button and a battery pack coupled to the lights; and a mounting mechanism for attachment to the existing screw locations of the SCBA mask.

3. The method according to claim 2, wherein the battery pack contains at least one battery.

4. The method according to claim 2, wherein the power button is a push button or pressure sensor is configured to be activated with a gloved hand.

5. The method according to claim 2, wherein the power supply is provided a control circuitry that powers down the strip of lights after a configurable or specified amount of time.

6. The method according to claim 5, wherein the control circuitry comprises a mechanism for adjusting the strip of lights.

7. The method according to claim 1, wherein the SCBA illumination system includes light emitting diodes.

8. The method according to claim 1, wherein the SCBA illumination System is supported proximate an upper edge of a facial opening of the SCBA mask.

9. The method according to claim 8, wherein the SCBA illumination system includes a strip of lights to provide a hands free light source directed forward to illuminate an area generally forward of the SCBA mask facial opening, or in whatever direction the SCBA mask facial opening is facing.

10. The method according to claim 8, wherein the SCBA mask facial opening includes a pane of substantially transparent material having a top molding piece extending along the upper edge, the SCBA illumination System being configured to attach proximate the top molding piece.

11. A method to modify a Self Contained Breathing Apparatus (SCBA) mask, comprising:

providing a Self Contained Breathing Apparatus (SCBA) illumination System, wherein the SCBA illumination system is configured to perform the same structural function as an existing part without affecting the SCBA mask's integrity, wherein the SCBA illumination System comprises:

a strip of light emitting diodes;

a power supply comprising a power button and a battery pack coupled to the lights; and a mounting mechanism for attachment to screw locations of the SCBA mask;

removing the existing part;

replacing the existing part with the SCBA illumination system; and securing the SCBA illumination system to the SCBA mask at the screw locations.

12. The method according to claim 11, wherein the existing part is a molding piece extending along at least an upper edge portion on the SCBA mask.

13. The method according to claim 11, wherein the existing part is a molding piece extending along at least a lower edge portion on the SCBA mask.

14. The method according to claim 11, wherein the existing part is a nose piece on the SCBA mask.

15. The method according to claim 11, wherein the strip of lights provide a hands free light source directed forward to illuminate an area generally forward of the of the SCBA mask facial opening or in multiple directions.

16. The method according to claim 11, wherein the battery pack contains at least one battery.

17. The method according to claim 11, wherein the power button is a push button or pressure sensor is configured to be activated with a gloved hand.

18. The method according to claim 11, wherein the power supply is provided a control circuitry that powers down the strip of light emitting diodes after a configurable or specified amount of time.

19. The method according to claim 18, wherein the control circuitry comprises a mechanism for adjusting the strip of light emitting diodes.

* * * * *